United States Patent [19]
Meyer

[11] Patent Number: 5,712,430
[45] Date of Patent: Jan. 27, 1998

[54] EXTENSOMETER STRUCTURE

[75] Inventor: Richard A. Meyer, Carver, Minn.

[73] Assignee: MTS Systems Corporation, Eden Prairie, Minn.

[21] Appl. No.: 730,789

[22] Filed: Oct. 16, 1996

[51] Int. Cl.[6] .................................................. G01N 3/08
[52] U.S. Cl. ............................ 73/831; 73/826; 73/760; 33/787
[58] Field of Search ........................... 73/790, 826, 781, 73/831, 782, 841, 760; 33/787

[56] References Cited

U.S. PATENT DOCUMENTS

| | | | |
|---|---|---|---|
| 3,319,338 | 5/1967 | De Nicola | 33/148 |
| 3,789,508 | 2/1974 | Meline | 33/148 D |
| 4,607,531 | 8/1986 | Meline | 73/794 |
| 4,841,226 | 6/1989 | Meline et al. | 324/61 R |
| 4,879,906 | 11/1989 | Meline et al. | 73/826 |
| 4,939,445 | 7/1990 | Meline et al. | 324/663 |
| 5,119,569 | 6/1992 | Meline | 73/831 |
| 5,463,902 | 11/1995 | Shrive et al. | 73/781 |
| 5,537,754 | 7/1996 | Bachmann et al. | 73/781 |
| 5,600,895 | 2/1997 | Meyer et al. | 73/841 |

*Primary Examiner*—Richard Chilcot
*Assistant Examiner*—Max H. Noori
*Attorney, Agent, or Firm*—Westman, Champlin & Kelly, P.A.; S. Koehler

[57] ABSTRACT

An extensometer structure for an extensometer includes a first extension arm, a second extension arm and a rigid support. A first hinge assembly joins the first extension arm to the rigid support. The first hinge assembly has a first pivot axis that allows the first extension arm to pivot relative to the rigid support about the pivot axis. A second hinge assembly joins the second extension arm to the rigid support. The second hinge assembly has a second pivot axis allowing the second extension arm to pivot relative to the rigid support about the second pivot axis.

16 Claims, 8 Drawing Sheets

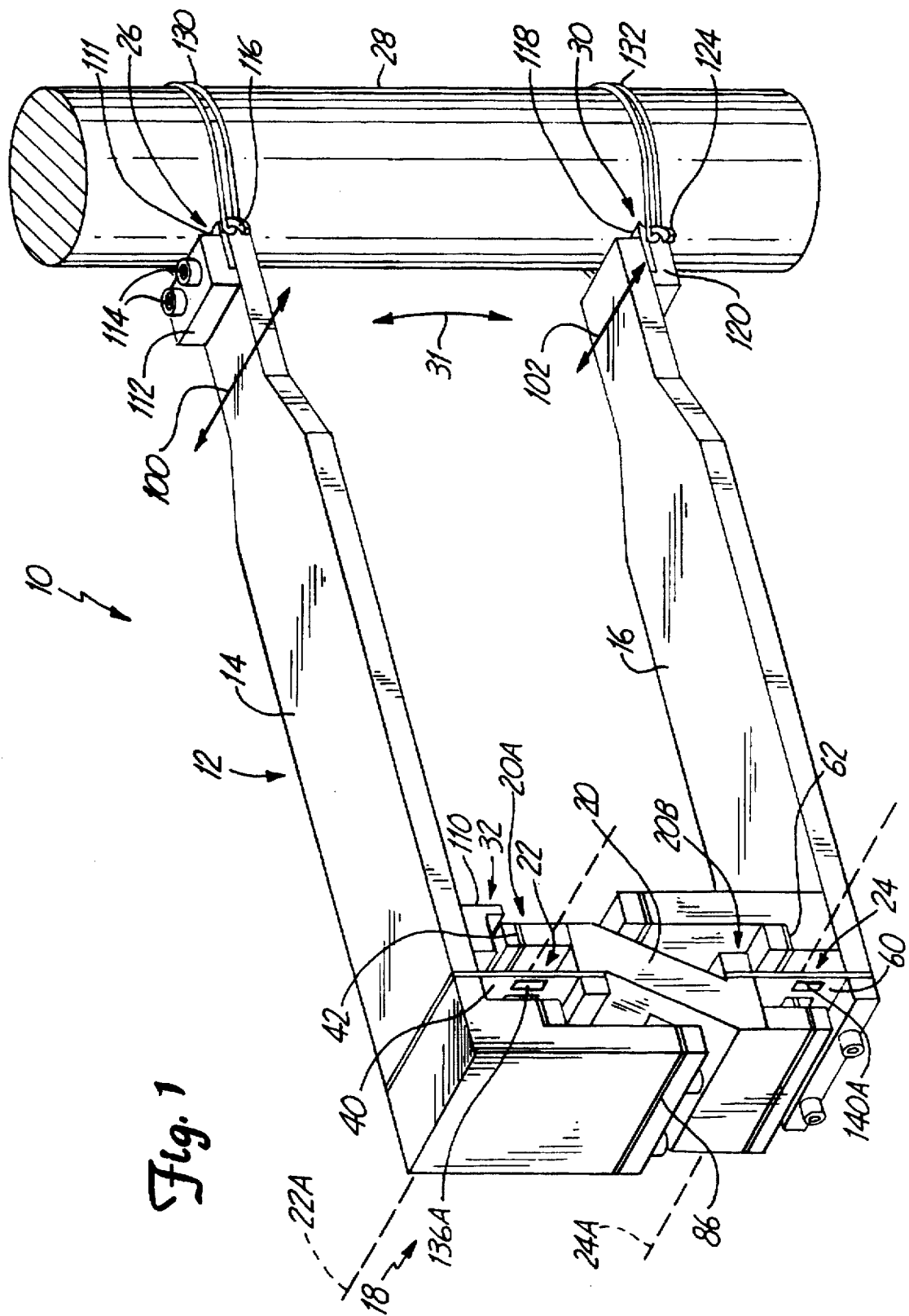

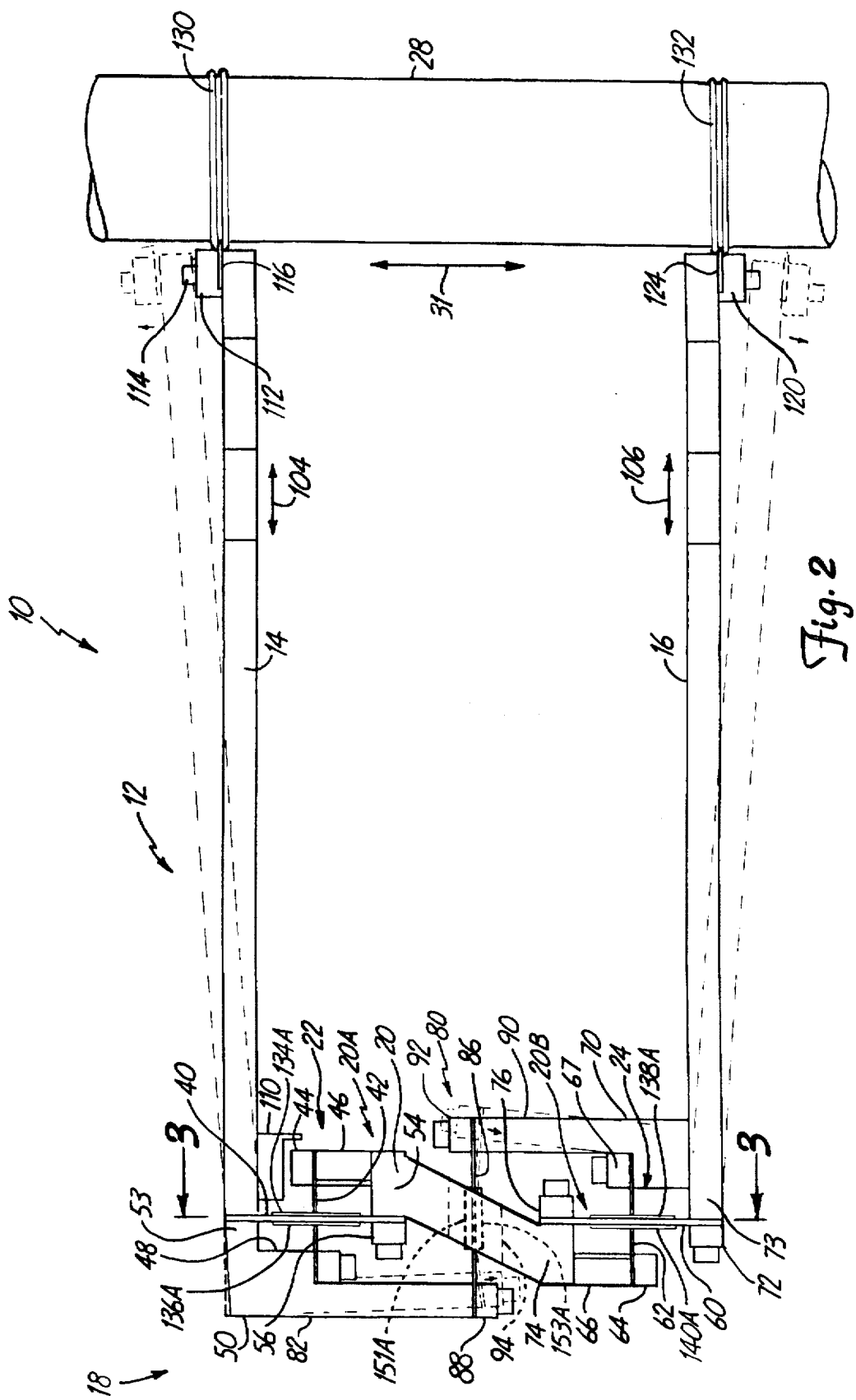

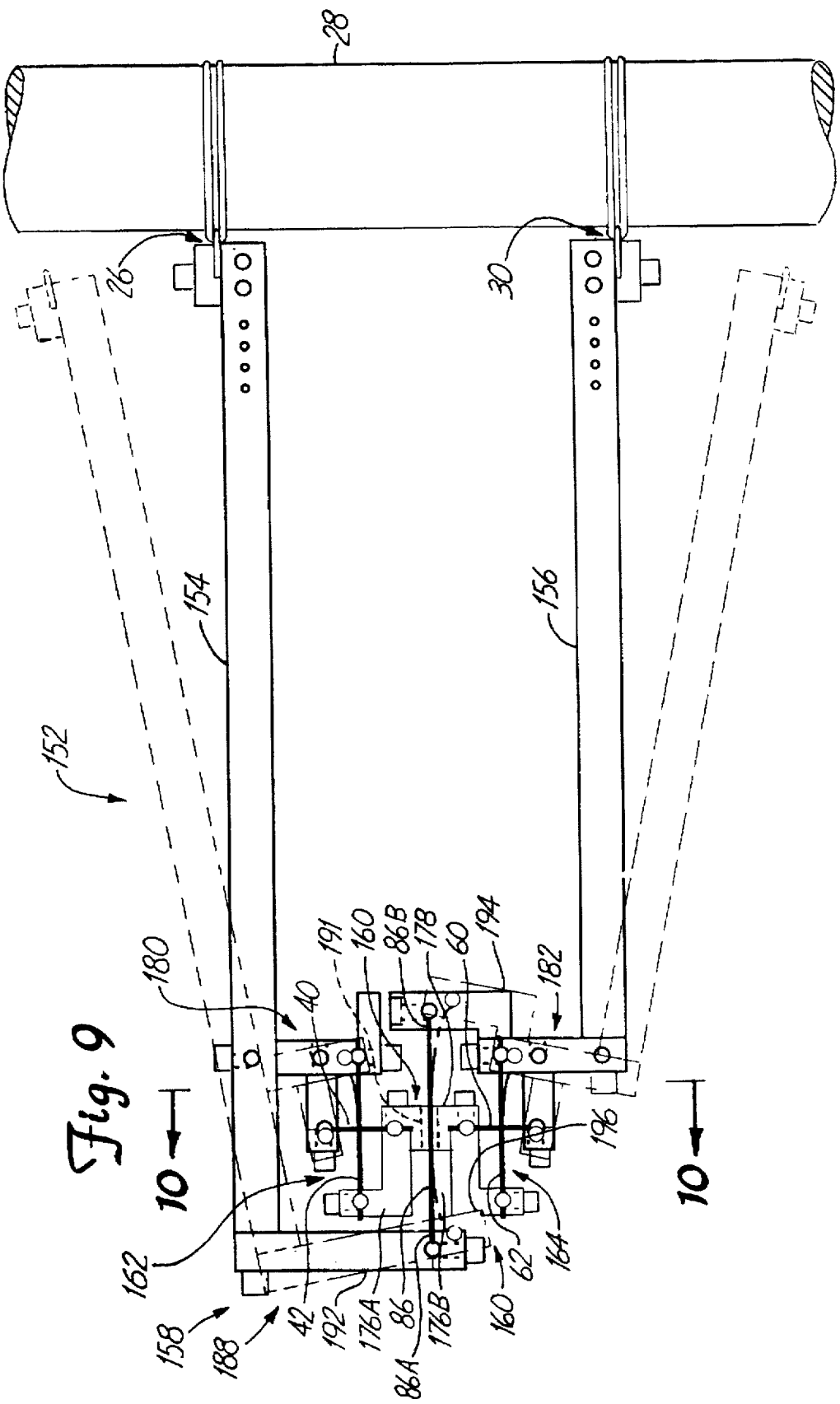

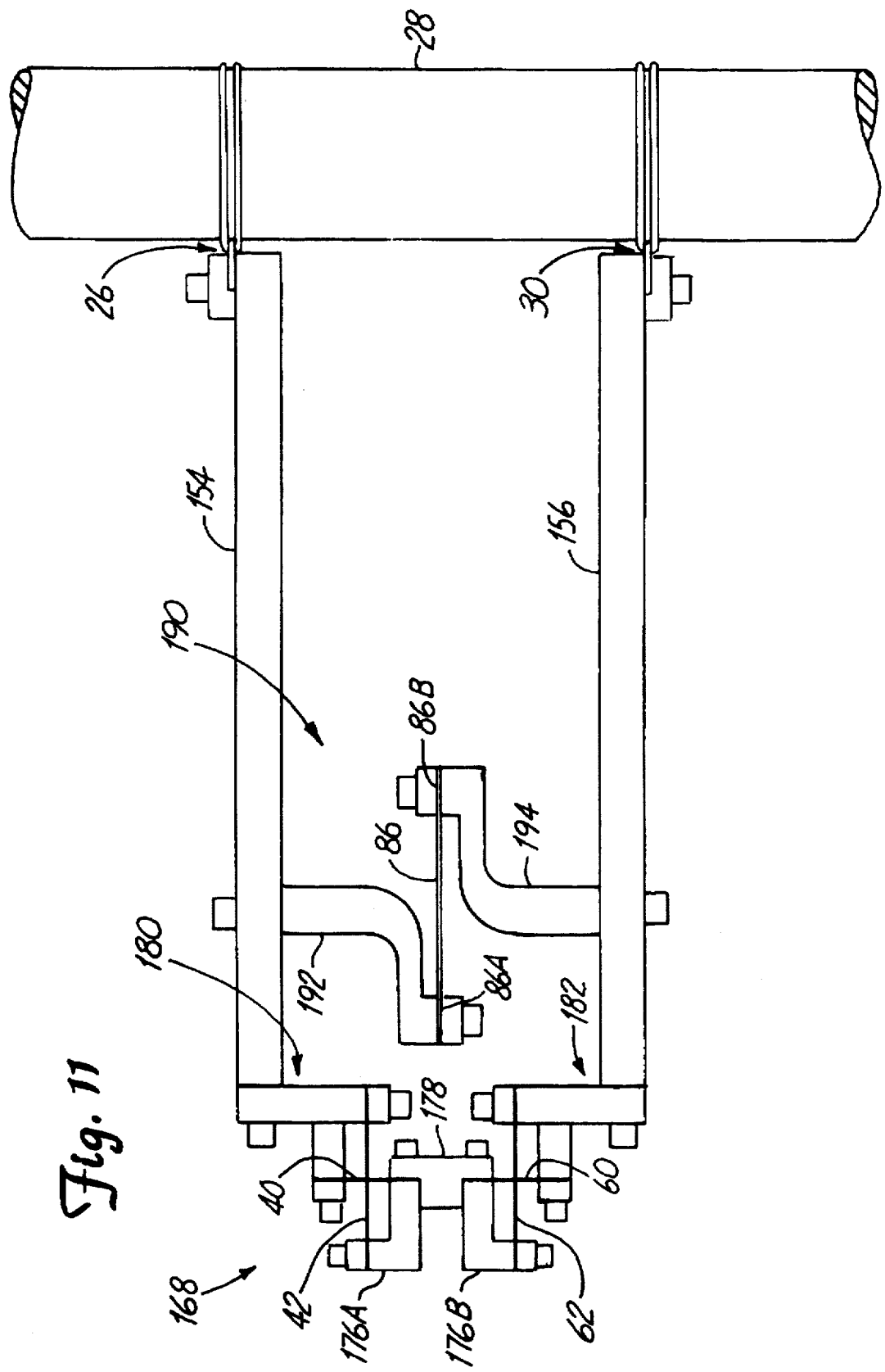

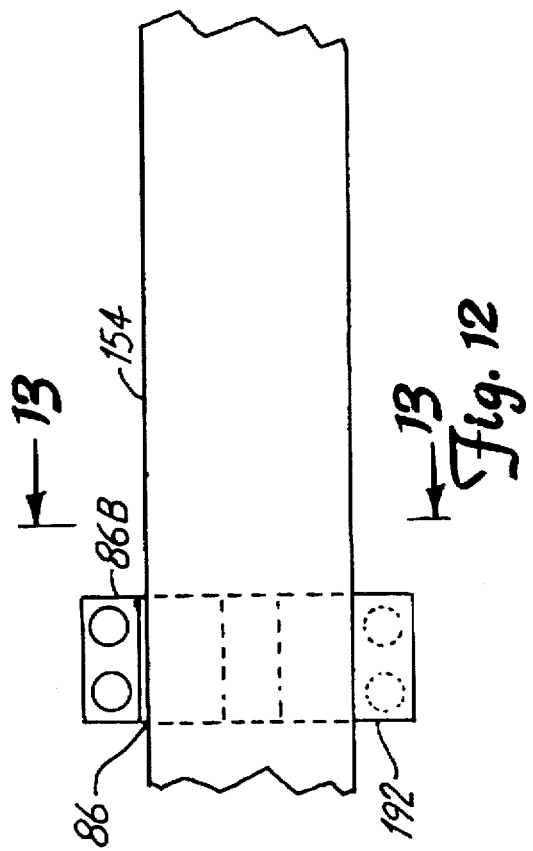
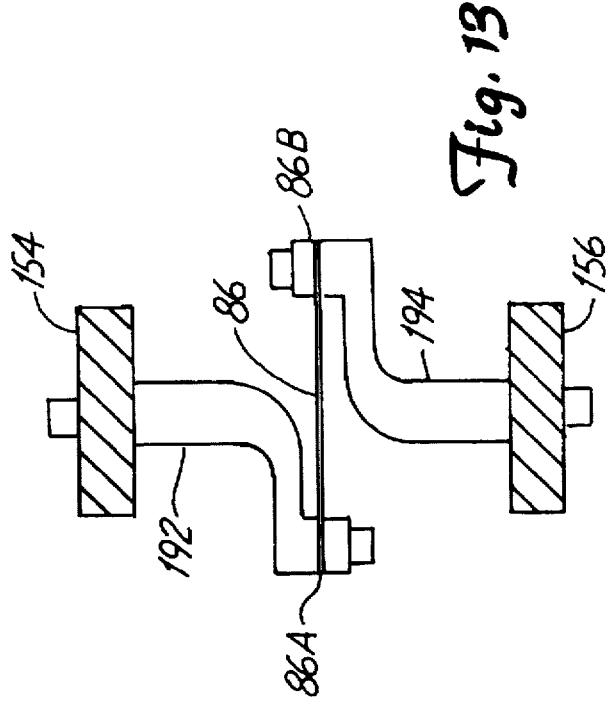

EXTENSOMETER STRUCTURE

BACKGROUND OF THE INVENTION

The present invention relates to an extensometer that measures a change in distance. More particularly, the present invention relates to an extensometer having an improved extensometer structure.

Extensometers are commonly used for measuring strain in a test specimen. Numerous forms of extensometers have been advanced in the art. One type of extensometer utilizes two extension arms held together by a cross-flexure mounting assembly as described and illustrated in U.S. Pat. No. 3,789,508. Flexure members of the cross-flexure mounting assembly form a pivot axis that allows the extension arms to pivot with respect to each other to measure strain in a test specimen. Although this form of an extensometer functions quite well, non-linearity of the output signal with respect to a change in distance of the extensometer arms is present due to the effective shortening of the extensometer arms as the arms pivot about the pivot axis. The effective shortening of the extensometer arms limits the useable range of travel of the extensometer. Therefore, there is a continuing need to increase the range of travel of an extensometer, while still maintaining substantial linearity of the output signal.

SUMMARY OF THE INVENTION

An extensometer structure for an extensometer includes a first extension arm, a second extension arm and a rigid support. A first hinge assembly joins the first extension arm to the rigid support. The first hinge assembly has a first pivot axis that allows the first extension arm to pivot relative to the rigid support about the first pivot axis. A second hinge assembly joins the second extension arm to the rigid support. The second hinge assembly has a second pivot axis that allows the second extension arm to pivot relative to the rigid support about the second pivot axis.

In a preferred embodiment, a bracing flexure assembly further couples the first extension arm to the second extension arm. The bracing flexure assembly includes a first support mounted to the first extension arm and a second support mounted to the second extension arm. A flexure member joins the first support to the second support. The bracing flexure assembly restrains the first extension arm and the second extension arm in unwanted shear displacement that could be reflected in the output signal, while still allowing substantially unrestrained pivotal motion about the pivot axes.

BRIEF DESCRIPTION OF THE DRAWINGS

FIG. 1 is a perspective view of a first embodiment of an extensometer of the present invention.

FIG. 2 is a side elevational view of the extensometer of FIG. 1.

FIG. 9 is a side elevational view of a second embodiment of an extensometer of the present invention.

FIG. 11 is a side elevational view of a third embodiment of an extensometer of the present invention with an alternate orientation of the bracing flexure assembly.

FIG. 12 is a partial top plan view of the extensometer of FIG. 11.

FIG. 13 is a sectional view taken along lines 13—13 of FIG. 12.

DETAILED DESCRIPTION OF THE PREFERRED EMBODIMENTS

Figure 10:
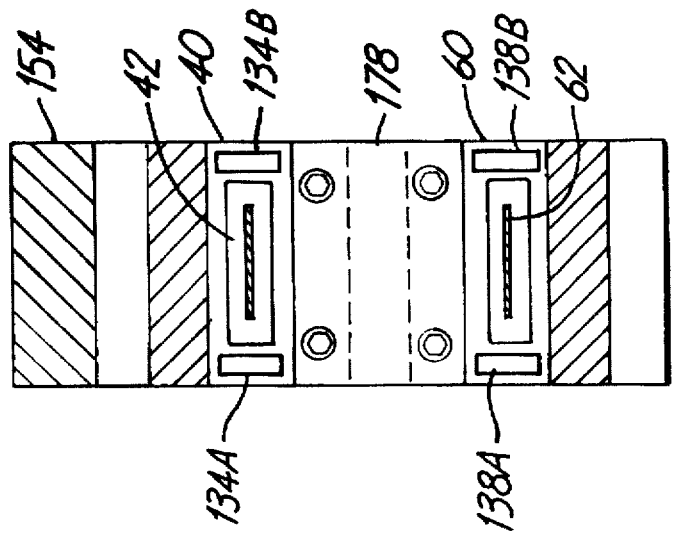
FIG. 10 is a sectional view taken along lines 10—10 of FIG. 9.

A first embodiment of an extensometer of the present invention is illustrated in FIGS. 1 and 2 at 10. The extensometer 10 includes an extensometer structure 12 of the present invention comprising a first extension arm 14 and a second extension arm 16 connected together by a hinge apparatus 18. The hinge apparatus 18 includes a rigid support 20 having a first end 20A and a second end 20B. A first hinge assembly 22 pivotally joins a distal end of the first extension arm 14 to the first end 20A of the rigid support 20. The first hinge assembly 22 has a first pivot axis 22A. The first extension arm 14 pivots relative to the rigid support 20 about the first pivot axis 22A. Similarly, a second hinge assembly 24 joins a distal end of the second extension arm 16 to the second end 20B of the rigid support 20. The second hinge assembly 24 has a pivot axis 24A. The second extension arm 16 pivots relative to the rigid support 20 about the second pivot axis 24A.

The first extension arm 14 includes a first tip 26 engageable with a test specimen indicated at 28. The second extension arm 16 includes a second tip 30 engageable with the test specimen 28. A sensing device 32, herein illustrated as a plurality of strain gauges 34 (for example, FIGS. 4 and 5), provides a signal representative of a change in distance between the tips 26 and 30 to a suitable display or recorder, not shown.

The hinge apparatus 18 allows independent relative movement of the first extension arm 14 and the second extension arm 16. When compared to prior art extensometers having the same length for the extensometer arms and a single hinge assembly coupling the extension arms together such as described in U.S. Pat. Nos. 3,789,508 and 4,939,445, the descriptions of which are incorporated herein by reference, the present invention provides two times the travel (indicated by double arrow 31) with the output signal from the sensing device 32 having substantially the same linearity as the prior art extensometers.

Preferably, each of the hinge assemblies 22 and 24 comprise conventional cross-flexure mounting assemblies. Referring to the first hinge assembly 22, the planes of resilient flexure members 40 and 42 intersect wherein the flexure member 42 passes through an opening 41 (FIG. 3) in the center of the flexure member 40. Referring to FIG. 2, one end of the flexure member 42 is clamped with a suitable clamp plate 44 to a portion 46 of the rigid support 20 that is substantially parallel to the flexure member 40. The other end of the flexure member 42 is clamped to the first extension arm 14 with a support member 50 having a portion 48 that is also substantially parallel to the flexure member 40. One end of the flexure member 40 is secured to the first extension arm 14 with the support member 50, while the other end of the flexure member 40 is clamped to a portion 54 of the rigid support 20 with a clamp plate 56. A portion 53 of the support 50 and the portion 54 of the rigid support 20 are substantially parallel to the flexure member 42.

The second hinge assembly 24 is similar to the first hinge assembly 22. The planes of resilient flexure members 60 and 62 intersect wherein the flexure member 62 passes through an opening 61 (FIG. 3) in the center of the flexure member 60. One end of the flexure member 62 is clamped with a suitable clamp plate 64 to a portion 66 of the rigid support 20 that is substantially parallel to the flexure member 60. The other end of the flexure member 62 is clamped to a support member 70 with a clamp plate 67. The support member 70 is secured to the second extension arm 16. One end of the flexure member 60 is secured to the second extension arm 16 with a clamp plate 72 fastened to a portion 73 of the second extension arm 16, while the other end of the flexure member 60 is clamped to a portion 74 of the rigid support 20 with a clamp plate 76.

Preferably, the flexure member 40 of the first hinge assembly 22, the flexure member 60 of the second hinge assembly 24, the pivot axis 22A and the pivot axis 24A are disposed substantially in the same plane.

Figure 3:
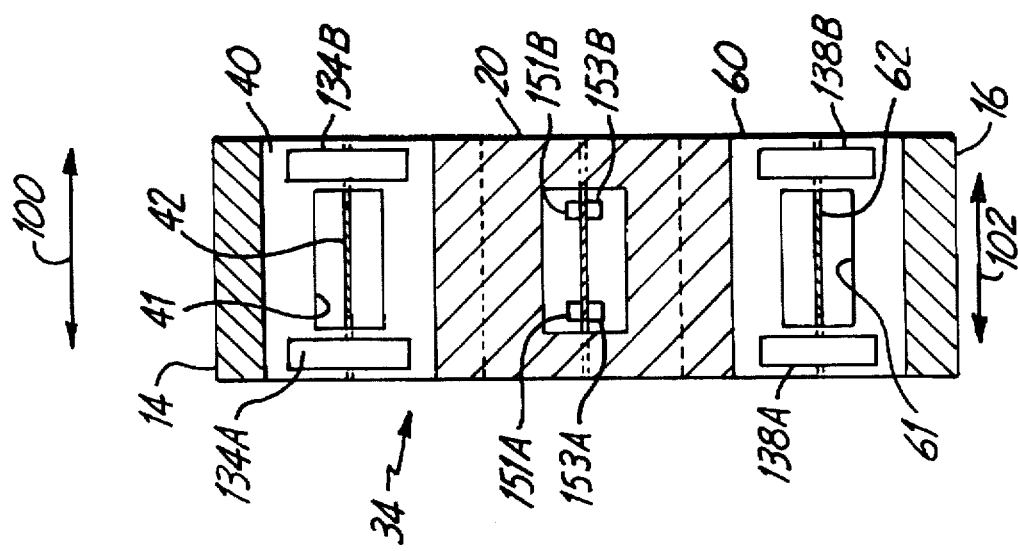
FIG. 3 is a sectional view taken along lines 3—3 in FIG. 2.

In a preferred embodiment, the first extension arm 14 and the second extension arm 16 are further coupled together with a bracing flexure assembly 80. In the embodiment illustrated, the bracing flexure assembly 80 includes a support portion 82 extending from the support member 50. A resilient flexure member or strip 86 is clamped to the support portion 82 with a clamp plate 88. The other end of the flexure member 86 is clamped to a support portion 90 with a clamp plate 92. The support portion 90 extends from the support member 70. Preferably, as illustrated in FIGS. 1–3, the flexure strip 86 extends through an aperture 94 provided in the rigid support 20. In this manner, the flexure strip 86 extends through, and preferably centered on, a plane defined by the pivot axes 22A and 24A. The bracing flexure assembly 80 restrains the extension arms 14 and 16 in lateral shear displacement, which as defined herein is opposed displacement of the extension arms 14 and 16 as indicated by double arrows 100 and 102 (FIG. 3). The bracing flexure assembly 80 also inhibits longitudinal shear displacement of the extension arms 14 and 16, which as defined herein is opposed displacement of the extension arms 14 and 16 as indicated by double arrows 104 and 106 (FIG. 2). Although illustrated wherein the flexure strip 86 extends through the aperture 94, it should be understood that the flexure strip 86 can be disposed along side the rigid support 20, or the rigid support 20 can extend through an aperture provided in the flexure strip 86.

In the embodiment illustrated, overtravel protection is provided with contact of the extension arms 14 and 16 with the rigid support 20. A stop 110 is secured to a lower surface of the extension arm 14. Contact of the stop 110 with the clamp plate 44 limits displacement of the extension arm 14 toward the extension arm 16. Displacement of the extension arm 16 toward the extension arm 14 is limited by contact of the clamp plate 92 with the rigid support 20. Displacement of the extension arm 14 away from the extension arm 16 is limited by contact of the clamp plate 88 with the rigid support 20, whereas displacement of the extension arm 16 away from the extension arm 14 is limited by contact of the clamp plate 72 with the clamp plate 64. If desired, additional overtravel protection can be secured to the extension arms 14 and 16 and can be provided adjacent the tips 26 and 30 as is known in the art.

Referring to FIG. 1, the first tip 26 is disposed on a knife-edge blade 111, typically used in the art, that is held in place on the first extension arm 14 with a holder or cap 112. The cap 112 is fastened with cap screws 114. The cap 112 further clamps a small wire clip 116 in place on the first extension arm 14. The second tip 30 is also disposed on a knife-edge blade 118 that is held on the second extension arm 16 with a cap 120. A wire clip 124 is positioned proximate the second tip 30 and is identical to the wire clip 116.

The knife-edge blades 111 and 118 are held in engagement with the test specimen 28 through the use of elastic rubber bands 130 and 132, respectively, which are hooked over the opposite ears of the wire clips 116 and 124. Of course, springs or other similar devices can be used in place of the bands 130 and 132. The elastic rubber bands 130 and 132 urge the tips 26 and 30 against the test specimen 28 such that when the test specimen 28 is strained in tension or compression, the first extension arm 14 and the second extension arm 16 will separate or move toward each other, respectively.

Figure 5:
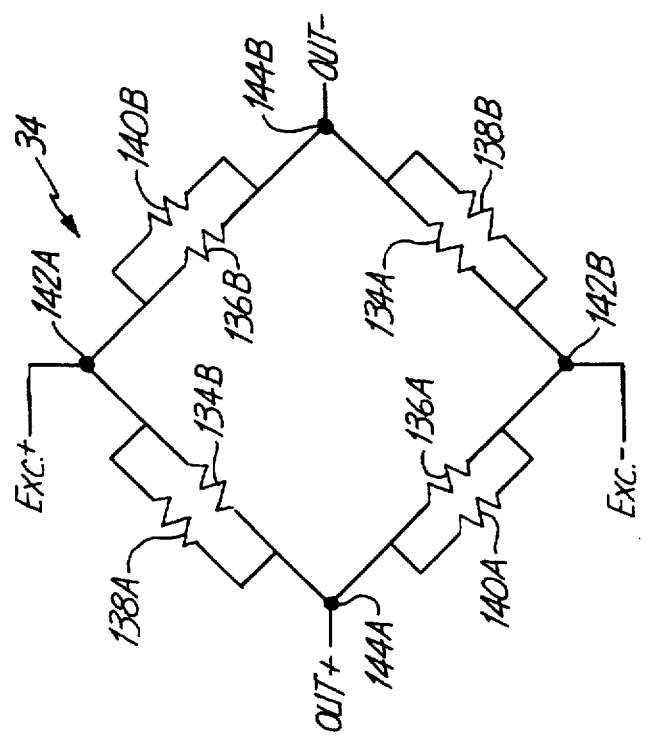
FIG. 5 is a second circuit diagram of a Wheatstone bridge.
Figure 4:
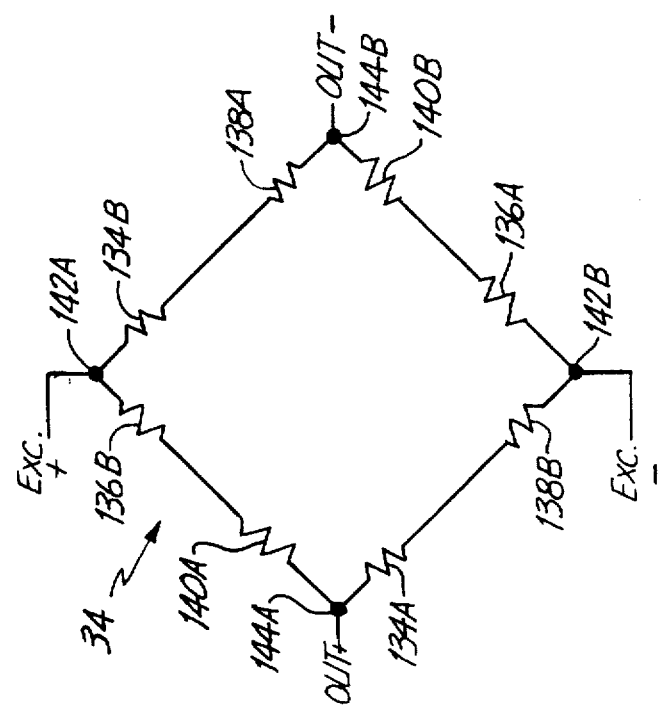
FIG. 4 is a first circuit diagram of a Wheatstone bridge.

In the embodiment illustrated, the strain gauges 34 are disposed on the flexure members 40 and 60. Referring also to FIGS. 3, 4 and 5, the strain gauges 34 are grouped in pairs to sense compression and tension in each of the flexure members 40 and 60. For measuring elongation of the test specimen 28, strain gauges 134A and 134B disposed on the flexure member 40 measure tension in the flexure member 40. A second set of strain gauges 136A and 136B are disposed on the opposite side of the flexure member 40 to measure compression of the flexure member 40. Similarly, strain gauges 138A and 138B sense tension in the flexure member 60, while strain gauges 140A and 140B disposed on an opposite side of the flexure member 60 from the strain gauges 138A and 138B sense compression of the flexure member 60. Of course, shortening of the test specimen 28 will result in the opposite effect in the flexure members 40, 42, 60 and 62.

FIGS. 4 and 5 illustrate suitable Wheatstone bridge circuits for interconnecting the strain gauges 134A, 134B, 136A, 136B, 138A, 138B, 140A and 140B to provide an output signal indicative of a change in distance between the tips 26 and 30. In FIGS. 4 and 5, excitation is provided at nodes 142A and 142B, while the output signal is obtained at nodes 144A and 144B.

Figure 6:
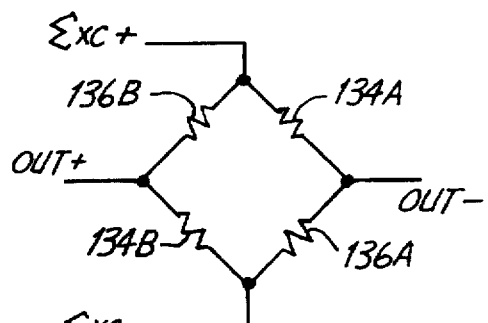
FIG. 6 is a third circuit diagram of a Wheatstone bridge.
Figure 7:
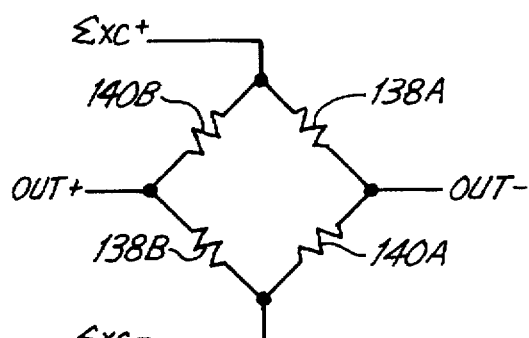
FIG. 7 is a fourth circuit diagram of a Wheatstone bridge.

FIG. 6 illustrates a separate Wheatstone bridge circuit for the strain gauges 134A, 134B, 136A and 136B, while FIG. 7 illustrates a separate Wheatstone bridge circuit for the strain gauges 138A, 138B, 140A and 140B. It should be understood that a change in distance between the tips 26 and 30 can be obtained using either of the circuits illustrated in FIGS. 6 or 7. Likewise, both of the circuits illustrated in FIGS. 6 and 7 can be used with the outputs added together.

Figure 8:
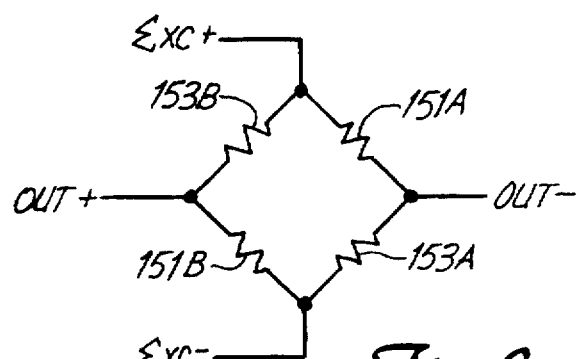
FIG. 8 is a fifth circuit diagram of a Wheatstone bridge.

It should be understood that strain gauges can be applied to the flexure members 42 and 62, if desired, to measure a change in distance between the tips 26 and 30. Likewise, strain gauges 151A, 151B, 153A and 153B can be applied to the flexure member 86, as illustrated in FIGS. 2 and 3, and connected as illustrated in FIG. 8, to measure a change in distance between the tips 26 and 30.

Although illustrated with strain gauges, other forms of sensing devices such as capacitive sensors can also be used.

FIGS. 9 and 10 illustrate a second embodiment of an extensometer structure 152 of the present invention. The extensometer structure 152 includes a first extension arm 154 and a second extension arm 156 connected together by a hinge apparatus 158. The hinge apparatus 158 includes a rigid support 160. A first hinge assembly 162 pivotally joins the first extension arm 154 to the rigid support 160, while a second hinge assembly 164 pivotally joins the second extension arm 156 to the rigid support 160. The hinge assemblies 162 and 164 include the flexure members 40, 42, 60 and 62, described above.

In this embodiment, the rigid support 160 is formed with legs 176A and 176B joined together with a cap 178. Supports 180 and 182 are joined to the extension arms 154 and 156, respectively. The flexure members 40 and 42 are secured to the support 180, while the flexure members 60 and 62 are secured to the support 182. A bracing flexure assembly 188 further couples the extension arms 154 and 156 together. The bracing flexure assembly 188 includes the flexure member 86, which extends through an aperture 191 in the rigid support 160. The flexure member 86 is supported at ends 86A and 86B by a support member 192 secured to the extension arm 154, and a support member 194 extending from the support 182, respectively.

In this embodiment, displacement of the extension arms 154 and 156 toward each other is limited by contact of the support 180 with the support 182. Displacement of the extension arm 154 away from the extension arm 156 is limited by contact of the support member 192 with the rigid support 160. A recess 196 is provided in the leg 176B to receive the support member 192.

Although illustrated in FIGS. 1, 2, 3, 9 and 10, where the flexure member 86 extends through the plane formed by the pivot axes of the hinge assemblies 22, 24, 162 and 164, it should be understood that a bracing flexure assembly can be mounted anywhere along the length of the extension arms. FIG. 11 illustrates a bracing flexure assembly 188 mounted between the hinge apparatus 168 and the tips 26 and 30. The bracing flexure assembly 188 includes the flexure member 86 and supports 192 and 194 joining opposite ends 86A and 86B of the flexure member 86 to the extension arms 154 and 156. The bracing flexure assembly 188, having the ends 86A and 86B substantially parallel to the extension arms 154 and 156, restrains the extension arms 154 and 156 in longitudinal shear displacement with some restraint provided in lateral shear displacement. If restraint in lateral shear displacement is required more than longitudinal shear displacement, the flexure member 86 and the supports 190 and 192 can be oriented perpendicular to the extension arms 154 and 156 as illustrated in FIGS. 12 and 13. Of course, the flexure member 86 of the extensometer structures 12 and 152 can extend through a suitable aperture in the rigid supports 20 and 160 to orient the flexure member 86 perpendicular to the extension arms 14, 16, 154 and 156, if desired.

Although the present invention has been described with reference to preferred embodiments, workers skilled in the art will recognize that changes may be made in form and detail without departing from the spirit and scope of the invention.

What is claimed is:

1. An extensometer structure for an extensometer, the extensometer structure comprising:

a first extension arm having a first tip engageable with a test specimen and a first distal end remote from the first tip;

a second extension arm having a second tip engageable with the test specimen and a second distal end remote from the second tip;

a rigid support having a first end and a second end;

a first hinge assembly joining the first distal end to the first end of the rigid support, the first hinge assembly having a first pivot axis allowing the first extension arm to pivot relative to the rigid support about the first pivot axis; and a second hinge assembly joining the second distal end to the second end of the rigid support, the second hinge assembly having a second pivot axis allowing the second extension arm to pivot relative to the rigid support about the second pivot axis.

2. The extensometer structure of claim 1 wherein each hinge assembly comprises a first resilient flexure extending in a first direction between the rigid support and the corresponding extension arm, and a second resilient flexure extending between the rigid support and the corresponding extension arm in a second direction transverse to the first direction.

3. The extensometer structure of claim 1 and further comprising a bracing flexure assembly joined to the first extension arm and the second extension arm to limit shear displacement of the first extension arm relative to the second extension arm.

4. The extensometer structure of claim 3 wherein the bracing flexure assembly comprises:

a first support mounted to the first extension arm;

a second support mounted to the second extension arm; and a flexure strip having a first end joined to the first support and a second end joined to the second support.

5. The extensometer structure of claim 4 wherein the flexure strip is oriented with the first end and the second end substantially parallel to the extension arms.

6. The extensometer structure of claim 4 wherein the flexure strip is oriented with the first end and the second end substantially perpendicular to the extension arms.

7. The extensometer structure of claim 4 wherein the rigid support includes an aperture, and wherein the flexure strip extends through the aperture.

8. The extensometer structure of claim 7 wherein each hinge assembly comprises a first resilient flexure extending in a first direction between the rigid support and the corresponding extension arm, and a second resilient flexure extending between the rigid support and the corresponding extension arm in a second direction transverse to the first direction.

9. The extensometer structure of claim 1 and further comprising sensing means for providing an output signal indicative of a distance between the first tip and the second tip.

10. The extensometer structure of claim 9 wherein the sensing means measures strain in the flexure strip.

11. The extensometer structure of claim 9 wherein the sensing means measures strain in the first resilient flexures.

12. An extensometer for measuring a change in distance between two points on a surface of a test specimen, the extensometer comprising:

a first extension arm having a first tip engageable with the test specimen and a first distal end remote from the first tip;

a second extension arm having a second tip engageable with the test specimen and a second distal end remote from the second tip;

a rigid support having a first end and a second end;

a first hinge assembly joining the first distal end to the first end of the rigid support, the first hinge assembly having a first pivot axis allowing the first extension arm to pivot relative to the rigid support about the first pivot axis;

a second hinge assembly joining the second distal end to the second end of the rigid support, the second hinge assembly having a second pivot axis allowing the second extension arm to pivot relative to the rigid support about the second pivot axis;

wherein each hinge assembly comprises a first resilient flexure extending in a first direction between the rigid support and the corresponding extension arm, and a second resilient flexure extending between the rigid support and the corresponding extension arm in a second direction transverse to the first direction;

sensing means for providing an output signal indicative of a distance between the first tip and the second tip; and a bracing flexure assembly joined to the first extension arm and the second extension arm to limit shear displacement of the first extension arm relative to the second extension arm.

13. The extensometer of claim 12 wherein the bracing flexure assembly comprises:

a first support mounted to the first extension arm;

a second support mounted to the second extension arm; and a flexure strip having a first end joined to the first support and a second end joined to the second support.

14. The extensometer of claim 13 wherein the flexure strip is oriented with the first end and the second end substantially parallel to the extension arms.

15. The extensometer of claim 13 wherein the flexure strip is oriented with the first end and the second end substantially perpendicular to the extension arms.

16. The extensometer of claim 13 wherein the rigid support includes an aperture, and wherein the flexure strip extends through the aperture.

* * * * *

UNITED STATES PATENT AND TRADEMARK OFFICE
CERTIFICATE OF CORRECTION

PATENT NO.    : 5,712,430
DATED         : January 27, 1998
INVENTOR(S)   : Meyer It is certified that error appears in the above-indentified patent and that said Letters Patent is hereby corrected as shown below:

```
Column 6, line 37, replace "1" with --8--.

Column 8, line 9, replace "13" with --14--.
```

Signed and Sealed this

Twenty-sixth Day of May, 1998

Attest:

BRUCE LEHMAN

Attesting Officer

Commissioner of Patents and Trademarks